United States Patent [19]

Schulman et al.

[11] Patent Number: 4,992,457
[45] Date of Patent: Feb. 12, 1991

[54] PHARMACOLOGICALLY ACTIVE CHOLINERGIC COMPOSITIONS, AND METHODS FOR MAKING SAME AND USE THEREOF IN TREATING DISEASE

[76] Inventors: Jerome M. Schulman, c/o City University of N.Y. at Queens College, Dept. of Chemistry, Kissena Blvd. Horace Harding Blvd., New York, N.Y. 11367; Raj K. Goyal, c/o Beth Israel Hospital, 330 Brookline Ave., Boston, Mass. 02215

[21] Appl. No.: 407,846

[22] Filed: Sep. 15, 1989

Related U.S. Application Data

[62] Division of Ser. No. 27,575, Mar. 18, 1987, Pat. No. 4,871,758.

[51] Int. Cl.$^5$ ................ C07D 233/60; A61K 31/415
[52] U.S. Cl. .................................. 514/376; 514/374; 514/397; 548/215; 548/225; 548/226; 548/227; 548/228; 548/229; 548/230; 548/336
[58] Field of Search .............. 548/215, 225, 226, 276, 548/336, 216, 227, 228, 229, 230; 514/374, 376, 370

[56]  References Cited

U.S. PATENT DOCUMENTS 3,853,852 12/1974 Eiter et al. ........................ 548/215

FOREIGN PATENT DOCUMENTS 0299513 7/1988 European Pat. Off. ............ 546/313

OTHER PUBLICATIONS

Chemical Abstract, vol. 94, No. 5, Abstract 29,658X, Feb. 2, 1981, p. 479.

Primary Examiner—Frederick E. Waddell
Assistant Examiner—Zinna Northington-Davis
Attorney, Agent, or Firm—Pennie & Edmonds

[57]  ABSTRACT

Compounds useful as cholinergic drugs are disclosed which have the formula A—B and pharmaceutically acceptable salts thereof having the formula $[(A-B)Q]+_qM^{-q}$ wherein M is a pharmaceutically acceptable anion, Q is a proton or lower alkylating group, q is an integer from 1 to 3, A is a saturated or unsaturated five- or six-membered heterocyclic moiety having the formula:

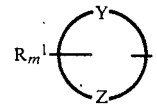

and B is a saturated or unsaturated five-membered heterocyclic moiety having the formula:

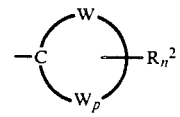

wherein $R^1$ and $R^2$ are each independently hydrogen, halo branched or straight-chain $C_1$–$C_6$ alkyl, branched or straight-chain $C_1$–$C_6$ haloalkyl, branched or straight-chain $C_1$–$C_6$ alkoxy, hydroxyl, keto or aryl; Y is —N= or

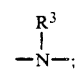

Z is —N=,

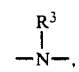

—O—, —S—,

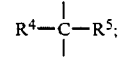

and $R^3$, $R^4$ and $R^5$ are each independently H, lower alkyl or aryl; W is —O—, —N=, or —S—; m is an integer from 1 to 5; n is an integer from 0 to 7; p is 0 or 1; and wherein, on a given molecule, when m is 2, or more, the $R^1$'s can be the same or different and two $R^1$'s can form a carbocyclic or heterocylic moiety fused onto adjacent positions of A and when P is 1, the two W's can be the same or different; and when n is 2 or more, the $R^2$'s can be the same or different and two $R^2$'s can form a carbocyclic or heterocyclic moiety fused onto adjacent positions of B. Pharmaceutical compositions useful in treating disorders of the central and peripheral nervous system of mammals, comprising an effective amounts of the aforesaid compounds, can be administered orally or intravenously.

4 Claims, No Drawings

PHARMACOLOGICALLY ACTIVE CHOLINERGIC COMPOSITIONS, AND METHODS FOR MAKING SAME AND USE THEREOF IN TREATING DISEASE

This is a division of application Ser. No. 027,575 filed Mar. 18, 1987, now U.S. Pat. No. 4,871,758.

BACKGROUND OF THE INVENTION

1. Technical Field

This invention relates to novel chemical compounds useful as cholinergic drugs, processes for preparing and pharmaceutical compositions containing such compounds, and methods for using them in the treatment of disease.

The invention further relates to novel compounds which act on cholinergic receptors of the central and peripheral nervous system. More particularly, it relates to certain compounds which are selective agonists and antagonists for subtypes of muscarinic cholinergic receptors, to processes for the preparation of such compounds, and to pharmaceutical compositions comprising them which can be used therapeutically for the treatment of diseases and disorders associated with such receptors in humans and animals.

2. Description of Background Art

Muscarinic pharmacological behavior was first distinguished from its nicotinic cholinergic counterpart by Dale in *J. Pharmacol. Exper. Ther.*, 6, 147–90 (1914). As used herein, the term "muscarinic cholinergic receptors" denotes that class of cholinergic receptors which are activated by acetylcholine and also by the alkaloid muscarine. Compounds such as muscarine which activate muscarinic receptors, in addition to binding strongly to them, are termed muscarinic "agonists" or muscarinic "cholinomimetics". Certain chemical compounds such as atropine bind to muscarinic cholinergic receptors but do not lead to a pharmacological response and, in fact, block the effects of acetylcholine and muscarinic agonists; they are termed muscarinic cholinergic "antagonists" or "cholinolytics". Finally, some compounds have less pharmacological potency than so-called "full" muscarinic agonists (i.e., those with unit intrinsic activity); they are termed "partial agonists". Muscarinic receptors are located on the smooth muscle and glands which they innervate. They are also found in ganglia and between neuronal synapses, and are generally located post-synaptically and/or pre-synaptically. Muscarinic cholinergic receptors can be visualized using radioactively-labeled muscarinic agonists or antagonists.

Heretofore, there has been much discussion in the neurosciences literature on muscarinic receptor subtypes analogous to alpha and beta adrenergic receptor subtypes and histamine H1 and H2 subtypes. Classification of muscarinic receptors into two subtypes, $M_1$ and $M_2$, has been proposed by Goyal and Rattan based upon the differentiating effects of partially selective agonists McN-A343 and bethanechol on the one hand, and the partially-selective antagonists pirenzepine and DAMP on the other. See Goyal et al., *Gastroenterology*, 74, 598–618 (1978). According to animal assay, $M_1$-activating behavior is associated with relaxation of the lower esophageal sphincter of an anaesthetized opossum; $M_2$-activating behavior is associated with contraction of the lower esophageal sphincter. This unique model has served well in the identification and localization of receptor subtypes of neurohormonal substances. See Goyal et al., supra, and Rattan et al., *J. Pharmacol. Exper. Ther.*, 224, 391–7 (1983).

Accordingly, it is an object of the present invention to provide chemical compounds which are highly selective agonists and antagonists for muscarinic receptor subtypes, and which are useful for clinical applications in the treatment of memory and cognitive disorders including such senile dementias as Alzheimer's disease, problems of gastrointestinal motility and secretion, cardiovascular problems and other disease conditions arising from and/or related to muscarinic cholinergic function or disfunction. The invention is also intended to provide chemical compounds which enhance and promote metal functions such as memory and coordination among healthy people. Yet another object is to provide methods for preparing the aforesaid compounds, pharmaceutical compositions containing them and procedures for administering the compounds to patients afflicted with the aforementioned disorders.

SUMMARY OF THE INVENTION

The foregoing objects are achieved according to the present invention by novel compositions of matter which are compounds having the general formula A—B, and pharmaceutically acceptable salts thereof having the general formula $[(A—B)Q]^+{}_q M^{-q}$. In these formulas, M is a pharmaceutically acceptable anion, Q is a proton or alkylating group, q is an integer from 1 to 3, A is a saturated or unsaturated five- or six-membered heterocyclic moiety having the formula:

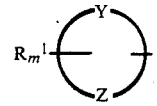

and B is a saturated or unsaturated five-membered heterocyclic moiety having the formula:

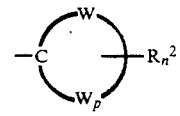

wherein $R^1$ and $R^2$ are each independently, hydrogen halo (e.g., fluoro, chloro, bromo and iodo), branched or straight-chain $C_1$–$C_6$ alkyl (e.g., methyl, ethyl, propyl, isopropyl, butyl, isobutyl, amyl, isoamyl and hexyl), branched or straight-chain $C_1$–$C_6$ haloalkyl, branched or straight-chain $C_1$–$C_6$ alkoxy, hydroxyl, keto or aryl (e.g., meta-chlorophenyl); Y is —N= or

Z is —N=,

—O—, —S—, or

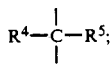

and $R^3$, $R^4$ and $R^5$ are each independently hydrogen, lower (i.e., branched or straight-chain $C_1$-$C_6$) alkyl or aryl (e.g., meta-chlorophenyl); W is —O—, —N= or —S—; m is an integer from 0 to 5; n is an integer from 0 to 7; and p is 0 or 1. On a given molecule, when m is 2 or more, the $R^1$'s can be the same or different and two $R^1$'s can form a carbocyclic or heterocyclic moiety fused onto adjacent positions of A; when p is 1, the two W's can be the same or different; and when n is 2 or more, the $R^2$'s can be the same or different and two $R^2$'s can form a carbocyclic or heterocyclic moiety fused onto adjacent positions of B. Pharmaceutically acceptable salts, $[(A-B) Q]^+{}_q M^{-q}$, include acid and quaternary salts derived from the above wherein Y is

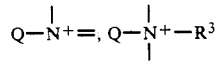

and Z is a neutral moiety, or wherein Y is a neutral moiety and Z is

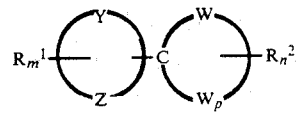

The moieties A and B are joined to each other by a single covalent bond so that the formula A—B becomes

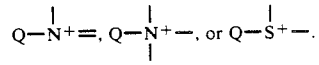

and the formula $[(A-B)Q]^+{}_q M^{-q}$ becomes

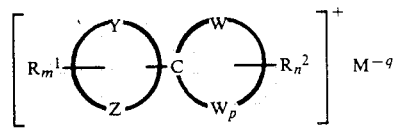

Among the moieties which A represents, the following are preferred:

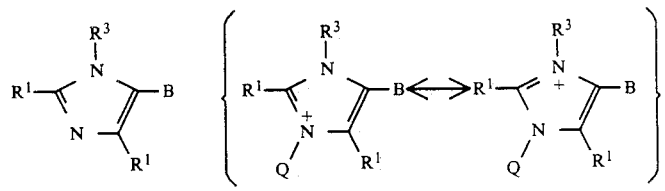

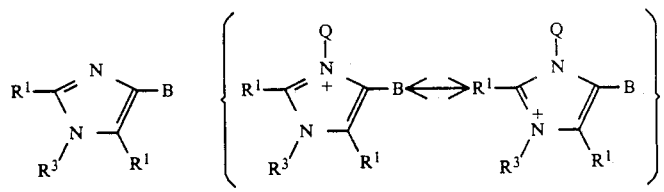

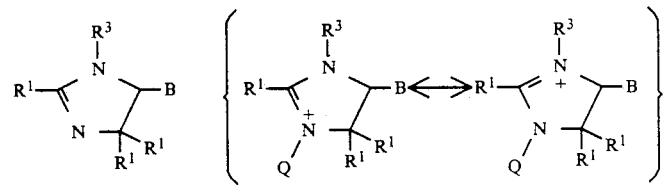

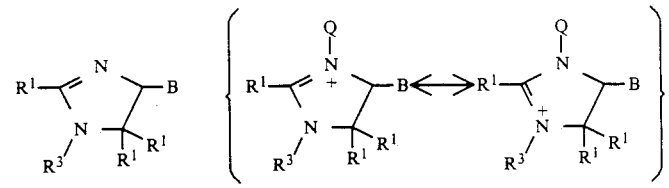

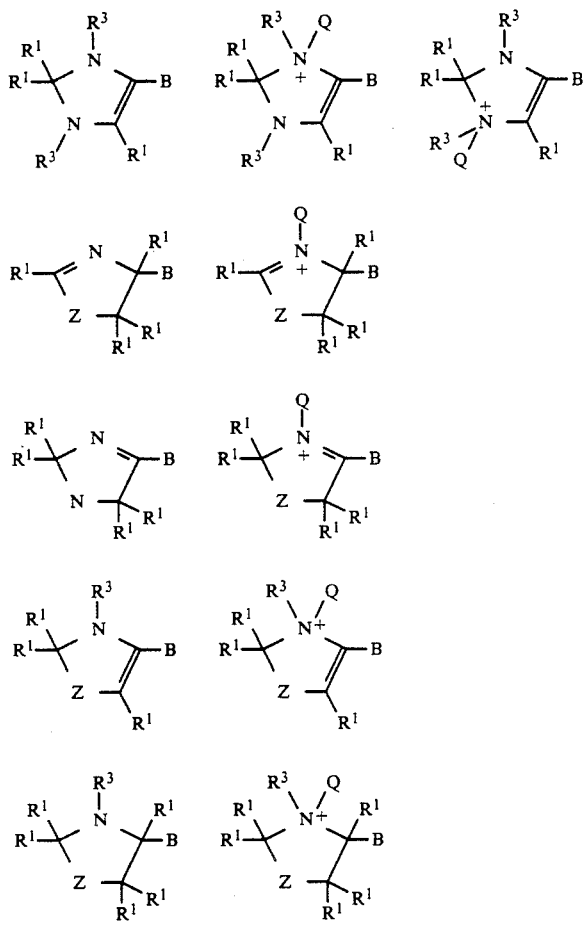

wherein Z is —O—, —N=, $$-\overset{R^3}{\underset{|}{N}}-,$$

—S—, or $$R^4-\overset{|}{\underset{|}{C}}-R^5,$$

and $R^1$, $R^3$, $R^4$ and $R^5$ are independently H or lower alkyl. When Q is H, the compounds are acid salts; when Q is lower alkyl, the compounds are quaternary salts.

Among the moieties which B represents, the following are preferred:

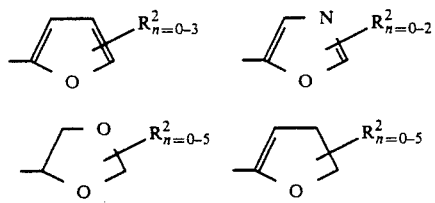

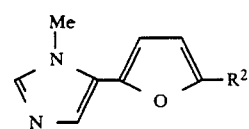

Optical (R and S) and diastereoisomers arising from chiral centers on the compounds, and racemates and mixtures thereof are within the scope of the invention.

Especially preferred among the compounds having the formulas A—B and $[(A—B)Q]^+_q M^{-q}$ are the following:

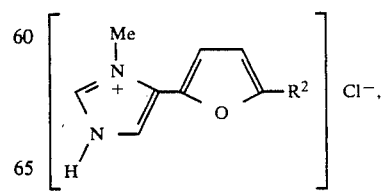

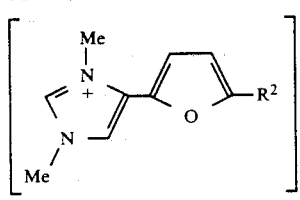

wherein $R^2$ is hydrogen or methyl.

The term "pharmaceutically acceptable salts" as used herein includes addition salts of strong or weak acids and hydrates thereof which are physiologically safe in mammals. Strong acids which form pharmaceutically acceptable salts with the foregoing compounds include, without limitation, hydrochloric, hydrobromic, hydroiodic, sulfuric and phosphoric acids. Weak acids which form pharmaceutically acceptable salts with the foregoing compounds include, without limitation, citric, tartaric, malic, fumaric and/or maleic acids. Pharmaceutically acceptable salts of the compounds of the invention may exist in anhydrous form as well as in solvated, including hydrated forms. In general, the hydrated forms and the solvated forms in pharmaceutically acceptable solvents are equivalent to the anhydrous or unsolvated form for the purposes of the invention.

The compounds according to invention can be prepared by several synthetic methods. One approach involves the following sequence of reactions:

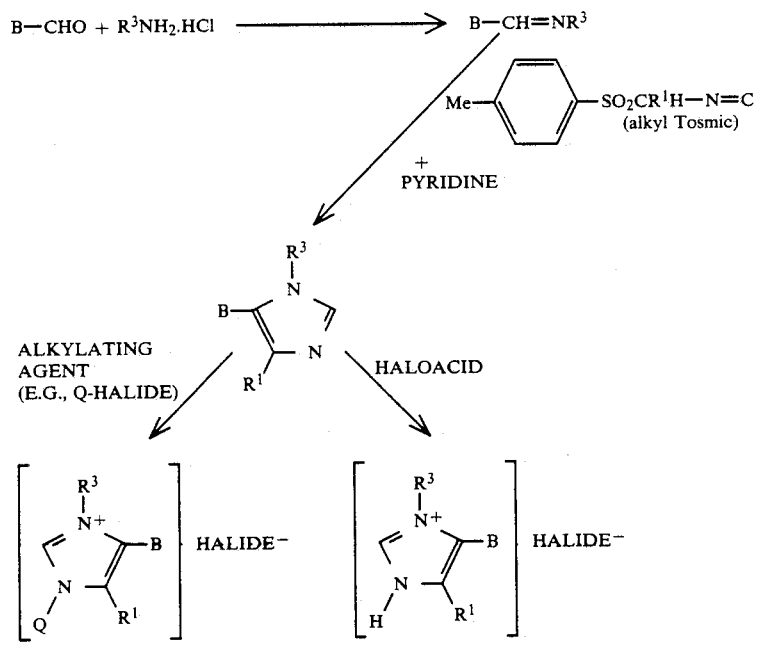

wherein $R^1$ is alkyl or aryl; Q is alkyl; $R^3$ is alkyl; and the halide can, if desired, be exchanged for a different pharmaceutically acceptable anion to give a salt of formula $[(A-B)Q]^+{}_q M^{-q}$.

The B—CHO reactant can be prepared according to the following exemplary procedures:

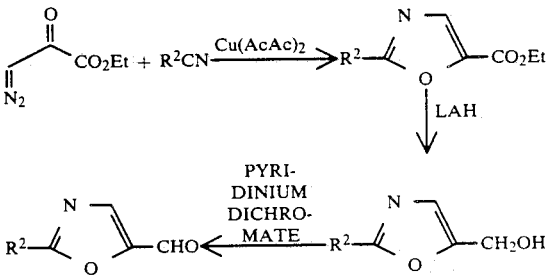

See M. E. Alonso et al., *J. Heterocycl. Chem.*, 17, 721 (1980)

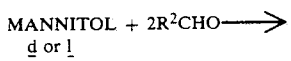

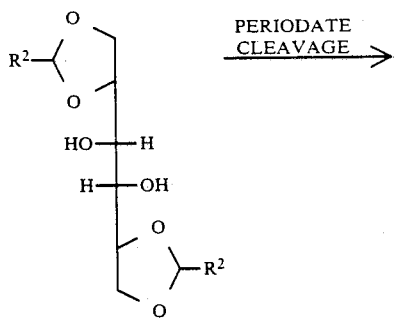

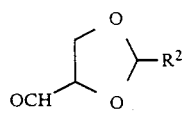

The two diastereoisomers can be separated by HPLC or column chromatography. The configuration at the carbon to which the aldehyde is attached is determined by the choice of d or l mannitol.

Another approach involves the following synthesis which is based upon the disclosure in Kempter et al., *J. Prakt. Chem.*, 313, 977-85 (1971):

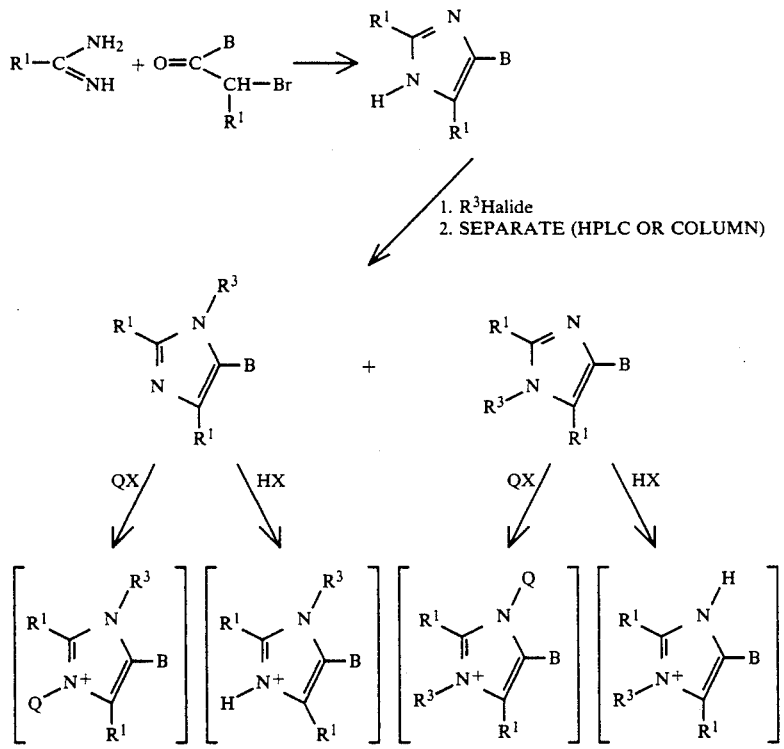

Schulman et al., *J. Med. Chem.*, 26, 817-23 (1983) describes a model (hereafter, "the model") of the binding of acetylcholine to muscarinic receptors. The model suggests that muscarinic agonists bind with muscarinic receptors in a conformational arrangement which enables the agonist cationic head group to interact with an anionic receptor locus along the local three-fold C(alpha)-N axis of the head group. Such binding action has since become known as "A-face approach". According to the model, the ether oxygen (i.e., the alcoholic oxygen of esters such as acetylcholine itself) simultaneously or soon thereafter interacts with a receptor site located approximately 1.2 angstroms from that oxygen. Also, several new geometric parameters, viz, a dihedral angle, PNOQ, and a distance, PQ, were defined. When the energetics of the conformations of various semi-rigid muscarinic agonists possessing a NCCOC backbone were subjected to analysis by a combination of molecular mechanics and ab initio quantum mechanical methods, it became possible to define the active conformations of acetylcholine and other muscarinic cholinergic agonists. During that period, it was suggested by Gieren and Kokkinidis in *Trends Pharmacol. Sci.*, 5, 369-70 (1984) that the cationic head group would interact with the receptor anionic site along a direction known as a "B-face". In that same publication, Schulman, et al., op. cit., 5, 75 (1984) pointed out that while the "B-face" approach was possible, the active conformations deduced assuming an A-face approach would, nonetheless, still hold. With both the A-face and B-face approaches in mind, one of the present inventors turned his attention to the muscarinic agonist pilocarpine, a plant-derived alkaloid. This agonist is unique in having an imidazolium group as the cationic head group. On the basis of these considerations, a new class of agonists has been designed which incorporate imidazolium-derived moieties or their analogs as the cationic part of the agonist and having suitable oxygen and terminal methyl-containing groups. One compound of particular interest is the furyl-N-methylimidazolium salt (I) having the following structure:

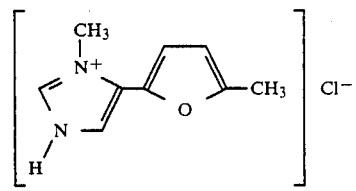

The muscarinic agonists of the present invention are believed to have specificity for muscarinic receptors of the $M_1$ subtype. Accordingly, they are useful for the therapy of senile dementia of the Alzheimer's-type. Without wishing to be bound by theory, it is believed that $M_1$ muscarinic receptors which are located post-synaptically in Alzheimer's patients remain intact while their $M_2$ receptors, located pre-synaptically and associated functionally with regulating the release of acetylcholine, are impaired. Thus $M_1$-selective agonists which mimic the behavior of acetylcholine when given as drugs, could augment any insufficiency in acetylcholine due to too few normally functioning synapses.

The compounds of the present invention which have $M_1$ properties (and also, possibly, some nicotinic properties which are useful when blending or fine-tuning of muscarinic and nicotinic properties is required) can be formulated into drug compositions which can be administered to normal humans with no known impairments in order to improve long and short-term memory function and to facilitate the development and utilization of acquired skills.

Administration of the pharmaceutical compositions of the invention can be effective elsewhere in the body. For example, in the gastrointestinal tract the compounds should improve gastrointestinal propulsion and therefore enhance esophageal, gastric, small bowel and colonic propulsive activity. Such prokinetic functions are responsive to $M_1$ receptor agonists. Therefore this agent may have therapeutic use in disorders of gastrointestinal transit. More generally, because muscarinic $M_1$ receptors are widely distributed in the body including cardiovascular, pulmonary, genitourinary, musculoskeletal, and endocrine systems, the compounds of the invention should be useful in treating those conditions where stimulation of $M_1$ muscarinic receptors will produce desirable effects.

Pharmaceutical compositions according to the present invention are formulated to take advantage of the fact that herein described cholinergic drugs are readily able to cross the blood-brain barrier so as to be effective upon the central nervous system when administered orally or intravenously. In formulating the present pharmaceutical compositions, at least one of the aforesaid therapeutic compounds of the formula A—B is admixed with one or more pharmaceutical carriers or excipients as may be appropriate for the desired mode of administration. For example, pharmaceutial compositions to be taken orally can be in the form of tablets, capsules or elixirs wherein the carrier or excipient can be milk sugar, starch or gelatin to name a few. For intravenous application, the pharmaceutical compositions can be formulated to include for example, water or saline.

In formulating the pharmaceutical compositions of the invention, it is desirable to formulate dosage units each being calculated to furnish a fixed dosage of active ingredient(s). It is sufficient to formulate the compositions so that the active ingredient(s) constitute an effective amount as determined in each case by the physician according to procedures well known to those skilled in the art. Preferably, an effective dose of the compounds of the invention ranges from $10^{-8}$ mole/kg to $10^{-4}$ mole/kg when administered intravenously. For oral administration, the corresponding dose ranges from $10^{-7}$ mole/kg to $10^{-4}$ mole/kg. At these levels, and because of the selectivity of the compounds of the invention, there are no toxicity or preclusive side effects.

DESCRIPTION OF PREFERRED EMBODIMENTS

Example 1

Preparation of 1-(N-methyl)-5-(5'-methyl-2'-furyl) imidazole

A quantity of 5-methylfurfural was condensed with methylamine (as a 40% aqueous solution) by a Mannich-type reaction to give the corresponding methylimine (5-methylfurfurylidene-N-methylimine), following the procedure set forth in Emling et al., J. Am. Chem. Soc., 71, 703 (1949). In the present example, 11.65 g (0.15 mole) of a 40% solution of methylamine in water was placed in a 125 ml Erlenmeyer flask containing a magnetic stirring bar and cooled and stirred in an ice-water bath. To this was added 11.01 g (0.1 mole) of 5-methyl-2-furanecarboxaldehyde dropwise over a period of 6 minutes to keep the temperature between 15° and 20° C. After 4 minutes additional cooling and stirring, the ice bath was removed and the amber mixture was then stirred at room temperature for thirty minutes (stoppered). The mixture was then re-cooled in ice-water and solid KOH pellets (9.25 g) were added over a period of four minutes to keep the temperature below 15° C. During this time, a lower aqueous layer and an amber upper organic layer were formed. The aqueous layer was extracted twice with 20 ml portions of methylene chloride and the extracts were combined with the organic layer, dried over solid KOH pellets (ca. 16 g), and allowed to stand at ambient temperature for one-half hour, and then concentrated under reduced pressure to give 12.08 g of brown oil. The following spectral data were obtained: Proton NMR (EM360, 207 mg/0.4 ml deuterochloroform and TMS); delta =2.37, singlet, 3H; 3.5, singlet, 3H; 6.1 broad doublet (J ca. 4 Hz), 1H; 6.63, broad doublet (J ca. 4 Hz), 1H; 8.03, doublet (J ca. 2 Hz), 1H. IR spectrum (5% carbon tetrachloride), (4 minute scan): no peaks above 3000 cm$^{-1}$ or 1680–1800 cm$^{-1}$; 2770 (sharp), 1643 (strong), 1587, 1530, 1450, 1432, 1400, 1381, 1368, 1343, 1275, 1263, 1229, 1201, 1124, 1020, 1002, 990, 968, 959, 953, 940, 662, 649 cm$^{-1}$ (0.1 mm cavity cells). Distillation of the clear amber mixture gave a major fraction boiling at 60.5° C. @9 mm Hg in the form of a clear colorless liquid which turned very slightly yellow in air. The next fraction boiled between 60.5° and 61.0° C. at 9 mm and was a clear, very faintly-yellow liquid. This fraction has essentially the same nmr spectrum as that described previously, and was used in the next step.

The methylimine described above was converted to 1-(N-methyl)-5-(5'-methyl-2'-furyl) imidazole having the following structure:

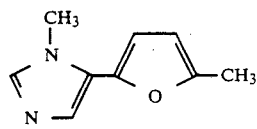

by reaction with p-toluenesulfonylmethylisocyanide (Tosmic) by the method taught in van Leusen et al., J. Org. Chem., 42, 1153 (1977). In the present example, a solution containing 3.08 g (0.025 mole) of the imine, 7.81 g (0.40 mol) of Tosmic, 6.91 g (0.05 mol) of anhydrous potassium carbonate, 50 ml of methanol and 100 ml of dimethoxyethane (glyme) was stirred magnetically for 17 hours in a stoppered 250 ml Erlenmeyer flask. The mixture was decanted from the solid potassium carbonate and evaporated to dryness under reduced pressure. A quantity (11.17 g) of brown-amber oil containing some solid was obtained. Instead of the methanol/-glyme solvent system, the synthesis can be carried out using pyridine according to the method of Miyashita et al., J. Org. Chem., 42, 3772 (1977).

Example 2

Preparation of 1-(N-methyl)-5-(5'-methyl-2'-furyl) imidazole, Hydrochloride

A quantity, (10.11 g; 0.0821 mole) of the imine prepared in Example 1 and 20.00 g (0.1025 mole) of Tosmic were dissolved in 100 ml dry pyridine and the solution was kept at room temperature for 10.5 days. The brown mixture was concentrated in a rotary evaporator under reduced pressure at 50° C. to give 18.58 g of a dark brown oil. The oil was dissolved in about 50 ml of methylene chloride and extracted three times with 10% HCl. The combined HCl extracts were back-washed twice with methylene chloride, then made basic with KOH pellets (with cooling). The basic mixture was extracted twice with 30-ml portions of methylene chloride. The combined extracts were dried over magnesium sulfate and concentrated under reduced pressure to give 6.88 g of a dark brown oil, smelling somewhat of pyridine. This was dissolved in 25 ml methylene chloride, cooled in ice and saturated with HCl gas to give the hydrochloride salt. A tan precipitate formed and part of the solid redissolved upon further HCl addition. The mixture was concentrated under reduced pressure to give 4.82 g of additional solid which was covered with about 30–50 ml methylene chloride, swirled and suction-filtered. The residue, weighing 3.907 g after methylene chloride rinse and air-drying, was a pale greenish yellow powder. A quantity (2.001 g) was dissolved in and recrystallized from 10 ml hot absolute ethanol after filtering the solution through charcoal to a golden-yellow color; cooling to room temperature gave yellow needles. Suction filtration and air drying gave 0.454 g of yellow needles, mp 239°–241° C., dec.

The nmr (64 mg/0.5 ml D20, 60 MHz) showed: delta=2.45, S, 3H; 4.04, S, 3H; 4.92 (NH or $H_2O$); 6.30, d, J=3.5 Hz, 1H (slightly broadened); 6.80, d, J=3.5 Hz, 1H; 7.63, d, J=1.5 Hz, 1H; 8.80 s (br). Irradiation at delta=2.45 converted the peak at 6.3 to a sharp doublet, J=3.5 Hz and also sharpened the peak at delta=6.8. Irradiation at delta=4.04 converted the peak at 8.80 to a sharp doublet, J=1.5 Hz, and also sharpened the doublet at delta=7.63. The assignments are the following: The peaks at 6.30 and 6.80 are the ring protons on the furan ring, the peak at 2.45 is the furan methyl group, the peaks at 7.63 and 8.80 are ring protons on carbons of the imidazole ring, 4.04 corresponds to the imidazole methyl group and the peak at 4.92 is the NH proton. The peaks at 7.63 and 8.80 are similar to their counterparts in pilocarpine.

A quantity (370 mg) of the yellow crystalline needles prepared above was redissolved in hot absolute ethanol, decolorized with charcoal, and recrystallized to give 158 mg of pale yellow needles, mp 239°–240° C., dec. This was vacuum-dried for 1.5 hours at room temperature. The following elemental analysis was obtained: %C, 54.74; %H, 5.65; %N, 13.67; %Cl, 17.60. This is consistent with the following structure:

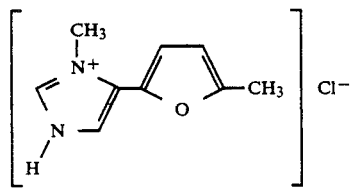

Example 3

The compound (I) obtained according to Example 2 was tested by assay on the lower esophageal sphincter of an opossum anaesthetized with sodium phenobarbitol. In carrying out the assay, the lower esophageal sphincter located between the esophagus and the stomach remains in a state of tonic contraction; therefore, a pressure sensing (manometric) catheter introduced from the animal's mouth into the lumen monitors lower esophageal sphincter pressures by registering a sustained high pressure zone, due to the lumen's myogenic contraction which is independent of neural or hormonal influences. Neural activity and hormones can increase or decrease the sphincter pressure and both excitatory and inhibitory influences can be readily detected.

The intraluminal pressures from the lower esophageal sphincter, esophageal body and the stomach are continuously monitored using a low compliance water-filled and continuously prefused catheter anchored in the lower esophageal sphincter so that artifacts due to axial motion can be minimized. See Goyal et al., *Gastroenterology*, 71, 62–7 (1976). All animals receive bilateral cervical vagotomy to eliminate vagally mediated changes in the sphincter pressure. Nerves to the sphincter are stimulated electrically by electrodes which are either applied to the distal end of the cut vagus nerve or applied intramurally in the sphincter. See Goyal et al., supra, and Rattan et al., *Am. J. Physiol.*, 234, E272–E276 (1978). Reflex relaxation of the sphincter is produced by distension of the esophagus with an intraluminal balloon. Drugs are administered in the arterial supply of the lower esophageal sphincter. This is done by opening the abdominal cavity and cannulating the artery that leads to the lower esophageal sphincter. The compound is injected into the blood supply of the lower esophageal sphincter and its effect therein is determined. The animal's vital signs are monitored and blood pressure is maintained with intravenous infusion of saline. Some drugs are administered intravenously.

In summary, the above-described model permits identification of muscarinic agonists and antagonists in a physiological system.

According to this procedure, it was determined that the compound I has only $M_1$ effects, i.e., it acts on the $M_1$ receptors on the intramural inhibitory neurons. Using this technique in the manner described below, it was found that compound I has a threshhold dosage of $10^{-8}$ mole/kg and a peak effect at a dosage of $10^{-6}$ mole/kg. A micromolar solution gave 80% of full agonist activity, indicating that it is a partial agonist. Its activity was found to be blocked by atropine. Compound I was tested on guinea-pig trachea and showed virtually no potency in contracting the trachea muscle; this result is consistent with the fact that those muscles have essentially $M_2$ receptors whereas compound I is highly selective for $M_1$ receptors.

The foregoing examples are intended to illustrate, without limitation, the compositions of the present invention, their preparation, and use thereof in treating disorders of the nervous system. It is understood that changes and variations can be made therein without departing from the scope of the invention as defined in the following claims.

We claim:

1. A compound useful as cholinergic drugs having the formula A—B or a pharmaceutically acceptable salt thereof having the formula $[(A—B) Q]^+ q\, M_{-q}$ wherein M is a pharmaceutically acceptable anion, Q is a proton or lower alkylating group, q is an integer from 1 to 3, A is

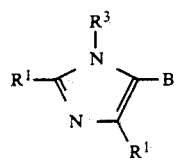

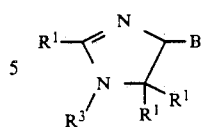

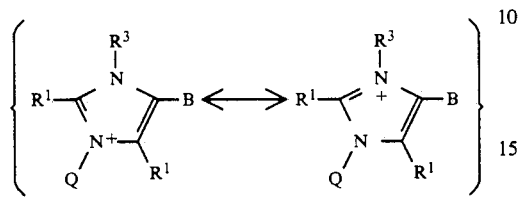

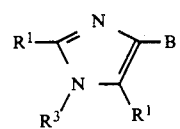

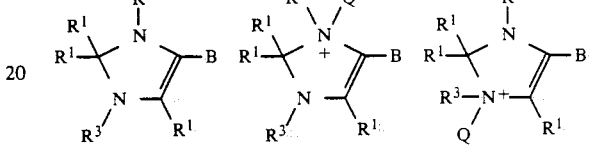

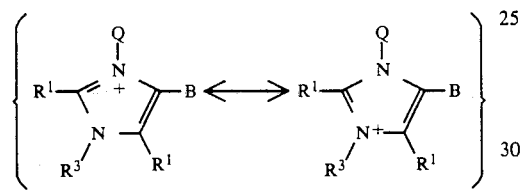

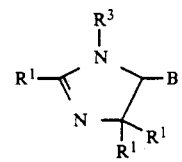

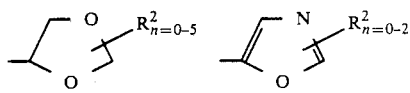

and B is wherein $R^1$ and $R^2$ are each independently hydrogen, halo, branched or straight-chain $C_1$–$C_6$ alkyl, branched or straight-chain $C_1$–$C_6$ haloalkyl, branched or straight-chain $C_1$–$C_6$ alkoxy, hydroxyl, keto or monocyclic aryl; and $R^3$ is H, lower alkyl or monocyclic aryl.

2. A compound according to claim 1 wherein $R^3$ is hydrogen or lower alkyl.

3. A pharmaceutical composition useful in treating disorders of the central and peripheral nervous system of mammals, comprising an effective amount of the compound of claim 1 and a pharmaceutically acceptable carrier.

4. A method of treating disorders of the central and peripheral nervous system of mammals, comprising administering thereto an effective amount of the pharmaceutical composition of claim 3.

* * * * *